United States Patent
Loftus-Vergari et al.

(10) Patent No.: US 10,850,372 B2
(45) Date of Patent: *Dec. 1, 2020

(54) APPARATUS FOR DRIVING A BONE FIXATION PIN

(71) Applicant: DEPUY SYNTHES PRODUCTS, INC., Raynham, MA (US)

(72) Inventors: Jeffrey Loftus-Vergari, West Chester, PA (US); Steven Krevitski, West Chester, PA (US); Kory Smith, West Chester, PA (US); Jeffrey Darrow, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,444

(22) Filed: Mar. 1, 2019

(65) Prior Publication Data

US 2020/0276689 A1    Sep. 3, 2020

(51) Int. Cl.
*B23B 31/12* (2006.01)
*B23B 23/00* (2006.01)
(Continued)

(52) U.S. Cl.
CPC ...... *B25B 23/0035* (2013.01); *B23B 31/1215* (2013.01); *B23B 51/12* (2013.01);
(Continued)

(58) Field of Classification Search
CPC ............ B23B 31/1207; B23B 31/1215; B23B 31/123; B23B 31/1253; B23B 31/005;
(Continued)

(56) References Cited

U.S. PATENT DOCUMENTS

| 246,513 A | 8/1881 | Ireland |
| 347,417 A | 8/1886 | Bullard |

(Continued)

FOREIGN PATENT DOCUMENTS

| DE | 3604927 A1 * | 8/1987 | ......... B23B 1/16158 |
| DE | 3604927 A1 | 8/1987 | |

OTHER PUBLICATIONS

Machine Translation, DE3604927 (A1), Muller et al., Aug. 20, 1987 (Year: 1987).*

(Continued)

*Primary Examiner* — Eric A. Gates
*Assistant Examiner* — Chwen-Wei Su
(74) *Attorney, Agent, or Firm* — Kramer & Amado, P.C.

(57) ABSTRACT

A bone fixation pin is inserted into a bone with an apparatus comprising a housing having a proximal portion and a distal portion, the distal portion having an inner surface and an opening configured to receive the bone fixation pin; a drive shaft having a proximal end configured to engage a handle and a distal end; and a body having an axis and a peripheral edge. The body comprises a bore along the axis, the bore being configured to slidably engage the distal end of the drive shaft; and a plurality of evenly spaced slots in the peripheral edge of the body. A plurality of chuck arms move radially along the evenly spaced slots in the peripheral edge of the body, each chuck arm having an inner surface and an outer surface. The distal end of the drive shaft and the body are within the proximal portion of the housing, the body being biased toward the distal end of the housing; and the inner surface of each chuck arm is configured to engage the bone fixation pin. The outer surface of each chuck arm slidably engages the inner surface of the housing.

7 Claims, 10 Drawing Sheets

(51) Int. Cl.
*B25B 23/00* (2006.01)
*B23B 51/12* (2006.01)
*B23B 31/00* (2006.01)

(52) U.S. Cl.
CPC ......... *B23B 31/005* (2013.01); *B23B 31/1253* (2013.01); *B23B 2260/136* (2013.01); *Y10S 279/906* (2013.01); *Y10T 279/17615* (2015.01)

(58) Field of Classification Search
CPC .............. B23B 51/12; B23B 31/16162; B23B 31/16166; B23B 31/16158; Y10T 279/17615; Y10T 279/17658; Y10S 279/906; A61B 17/7076; B25B 23/0035
See application file for complete search history.

(56) References Cited

U.S. PATENT DOCUMENTS

| | | |
|---|---|---|
| 1,054,238 A | 2/1913 | Powers |
| 2,172,070 A | 3/1938 | Palmgren |
| 2,553,990 A | 1/1948 | Vidal |
| 2,896,957 A | 7/1959 | Vermette |
| 3,520,545 A | 7/1970 | Tripp |
| 3,692,321 A | 9/1972 | Shattuck |
| 3,718,340 A | 2/1973 | Stewart |
| 4,266,789 A | 5/1981 | Wahl et al. |
| 4,463,960 A | 8/1984 | Walton |
| 4,491,445 A * | 1/1985 | Hunger ................ B23B 31/123 409/234 |
| 4,609,199 A * | 9/1986 | Rohm ................... B23B 31/123 173/211 |
| 4,848,779 A | 7/1989 | Wheeler et al. |
| 5,180,261 A | 1/1993 | Schreiber |
| 5,375,489 A | 12/1994 | McClure |
| 6,505,840 B2 | 1/2003 | Huggins et al. |
| 6,648,563 B2 | 11/2003 | Rohm |
| 7,316,404 B1 | 1/2008 | Walker |
| 8,308,168 B2 | 11/2012 | Nash |
| 9,283,625 B2 | 3/2016 | Thorson et al. |
| 2016/0031017 A1 | 2/2016 | Peters et al. |
| 2019/0111555 A1* | 4/2019 | Abbott ................ B25D 17/084 |

OTHER PUBLICATIONS

Non-Final Office Action dated Mar. 31, 2020 in U.S. Appl. No. 16/439,185, filed Jun. 12, 2019.

* cited by examiner

APPARATUS FOR DRIVING A BONE FIXATION PIN

BACKGROUND

1. Field of the Disclosure

This disclosure relates generally to devices for positioning bone fixation pins or screws in a bone. More particularly, this disclosure relates generally to devices for positioning bone fixation pins or screws having differing diameters in bones using a single tool.

2. Description of Related Art

Bone fixation pins, screws, and the like are produced in a variety of diameters. Such pins are positioned in a bone, or used to hold multiple bones or bone fragments together. Such pins or screws are manipulated using chucks having movable chuck arms which grip the shaft of a pin or screw.

In a surgical environment, it is desirable to be able to quickly insert and remove bone fixation pins or screws from a chuck, without spending time manipulating the chuck to ensure that the chuck arms properly grip the pin. Further, it is often necessary to use multiple pins having different diameters in a single procedure or a single operation. A single chuck which can accommodate pins having a variety of diameters would save time in the operating theater, as the operating team would not have to ensure that the proper chuck is matched to each pin.

A variety of adjustable chucks are known in the art. However, many of these chuck arms require manipulation of the chuck body to open or close the chuck arms. In some cases, the inner surface of the chuck body has threading which mates with threading provided on the outer surfaces of the chuck arms. Rotation of the chuck body then causes axial movement of the chuck arms. In other cases, the chuck arms engage an inner surface of the chuck body, so axial movement of the chuck body causes radial movement of the chuck arms. However, it would be preferable to position a bone fixation pin on a chuck quickly, without requiring manual manipulation of the chuck.

SUMMARY

In light of the present need for improved tools or chucks for manipulating bone fixation pins or screws, a brief summary of various embodiments is presented. Some simplifications and omissions may be made in the following summary, which is intended to highlight and introduce some aspects of various embodiments, but not to limit the scope of the invention. Detailed descriptions of various embodiments adequate to allow those of ordinary skill in the art to make and use the inventive concepts will follow in later sections.

Various embodiments disclosed herein relate to an apparatus for inserting a bone fixation pin having a rounded, conical, or frustoconical head and a cylindrical body into a bone. The apparatus includes a housing having a proximal portion and a distal portion, the distal portion having a conical inner surface and an opening configured to receive the bone fixation pin; a drive shaft having a proximal end configured to engage a handle and a distal end; and a body having an axis and a peripheral edge. The body includes a bore along the axis of the body, where the bore may slidably engage the distal end of the drive shaft; and a plurality of evenly spaced slots in a peripheral edge of the body. A plurality of chuck arms, each chuck arm is adapted to move radially along one of the evenly spaced slots in the peripheral edge of the body, with chuck arm having an inner surface and an outer surface. In various embodiments, the distal end of the drive shaft and the body are within the proximal portion of the housing, with the body being biased toward the distal end of the housing by a biasing force. In various embodiments, the biasing force is applied by a spring. The inner surface of each chuck arm is configured to engage the bone fixation pin, and the outer surface of each chuck arm slidably engages the conical inner surface of the housing. In various embodiments, the proximal end of the drive shaft has a conical or frustoconical opening configured to receive the rounded, conical, or frustoconical head of the bone fixation pin.

In various embodiments, the inner surface of each chuck arm comprises a sloped lower surface configured to engage the rounded, conical, or frustoconical head of the bone fixation pin; and an upper surface parallel to the axis of the body. The upper surface is configured to engage the cylindrical body of the bone fixation pin. The apparatus is configured to receive a bone fixation pin through the opening in the housing until the head of the pin engages the opening in the proximal end of the drive shaft. Contact between the head of the bone fixation pin and the sloped lower surfaces of the chuck arms then pushes the chuck arms radially outward in the slots in the peripheral edge of the body; and radial movement of the chuck arms causes the chuck arms to slidably move along the conical inner surface of the housing, pushing the body axially toward the proximal end of the housing, until the bone fixation pin is held in position by the inner surfaces of the chuck arms and the force biasing the body toward the distal end of the housing.

Various embodiments disclosed herein relate to an apparatus for inserting a bone fixation pin into a bone, the pin having a rounded, conical, or frustoconical head and a cylindrical body having a body diameter. The apparatus includes a housing having a proximal portion and a distal portion, the distal portion having a stepped inner surface and an opening configured to receive the bone fixation pin. Each step in the stepped inner surface may have a lower edge which is sloped toward an axis of the housing; and an inner edge having a surface which is parallel to the axis of the housing. The apparatus further includes a drive shaft having a proximal end configured to engage a handle and a distal end; and a body having an axis and a peripheral edge. The body includes a bore along the axis, said bore being configured to slidably engage the distal end of the drive shaft; and a plurality of evenly spaced slots in the peripheral edge of the body. The evenly spaced slots are configured to receive a plurality of chuck arms, where each chuck arm is adapted to move radially along one of the evenly spaced slots in the peripheral edge of the body. Each chuck arm has an inner surface and a lower tip. The distal end of the drive shaft and the body are within the proximal portion of the housing, said body being biased toward the distal end of the housing, possibly by a spring. The inner surface of each chuck arm is configured to engage the bone fixation pin, and the lower tip of each chuck arm slidably engages a first step on the stepped inner surface of the housing.

In various embodiments, the proximal end of the drive shaft has a conical or frustoconical opening configured to receive the head of the bone fixation pin. The inner surface of each chuck arm comprises a sloped lower surface configured to engage the rounded, conical, or frustoconical head of the bone fixation pin; and an upper surface parallel to the axis of the body, the upper surface being configured to engage the cylindrical body of the bone fixation pin. In various embodiments, the apparatus is configured to receive a bone fixation pin through the opening in the housing until the head of the pin engages the opening in the proximal end of the drive shaft. Contact between the head of the bone fixation pin and the sloped lower surfaces of the chuck arms pushes the chuck arms axially toward the proximal end of the housing. In various embodiments, this axial movement causes the lower tip of each chuck arm to disengage from the first step on the stepped inner surface of the housing and engage a second step on the stepped inner surface. The chuck arms are configured to engage the cylindrical body of the bone fixation pin when the lower tip of each chuck arm engages the second step on the stepped inner surface.

In various embodiments, the stepped inner surface of the housing comprises a second step and a third step, the second and third steps being configured to be sequentially engaged by the lower tip of each chuck arm as the chuck arms move toward the proximal end of the housing. The chuck arms are configured to engage the cylindrical body of a bone fixation pin having a first body diameter when the lower tip of each chuck arm engages the second step on the stepped inner surface; and to engage the cylindrical body of a bone fixation pin having a second body diameter when the lower tip of each chuck arm engages the third step on the stepped inner surface.

Various embodiments of the various devices for inserting a bone fixation pin may include a release member, where the release member is configured to disengage the bone fixation pins or screws upon movement of the release member in a proximal direction.

BRIEF DESCRIPTION OF THE DRAWINGS

In order to better understand various exemplary embodiments, reference is made to the accompanying drawings, wherein.

DETAILED DESCRIPTION

This disclosure described a tool or chuck which receives a bone fixation pin or screw having a shaft, where the shaft may have any of a variety of diameters. The improved chuck includes a plurality of chuck arms which expand radially to grip the shaft of a bone fixation pin or screw without requiring any manipulation of a chuck body or housing by a user. After insertion into a bone, the pin or screw may be withdrawn from the chuck axially, at which point the chuck or tool may receive a second pin or screw having the same diameter or a different diameter.

The foregoing advantages are illustrative of those that can be achieved by the various embodiments disclosed herein and are not intended to be exhaustive or limiting of the possible advantages which can be realized. Thus, these and other advantages of the various embodiments disclosed herein will be apparent from the description herein or can be learned from practicing the various disclosed embodiments, both as embodied herein or as modified in view of any variation that may be apparent to those skilled in the art. Accordingly, the present invention resides in the novel methods, arrangements, combinations, and improvements herein shown and described in various embodiments.

Figure 1:
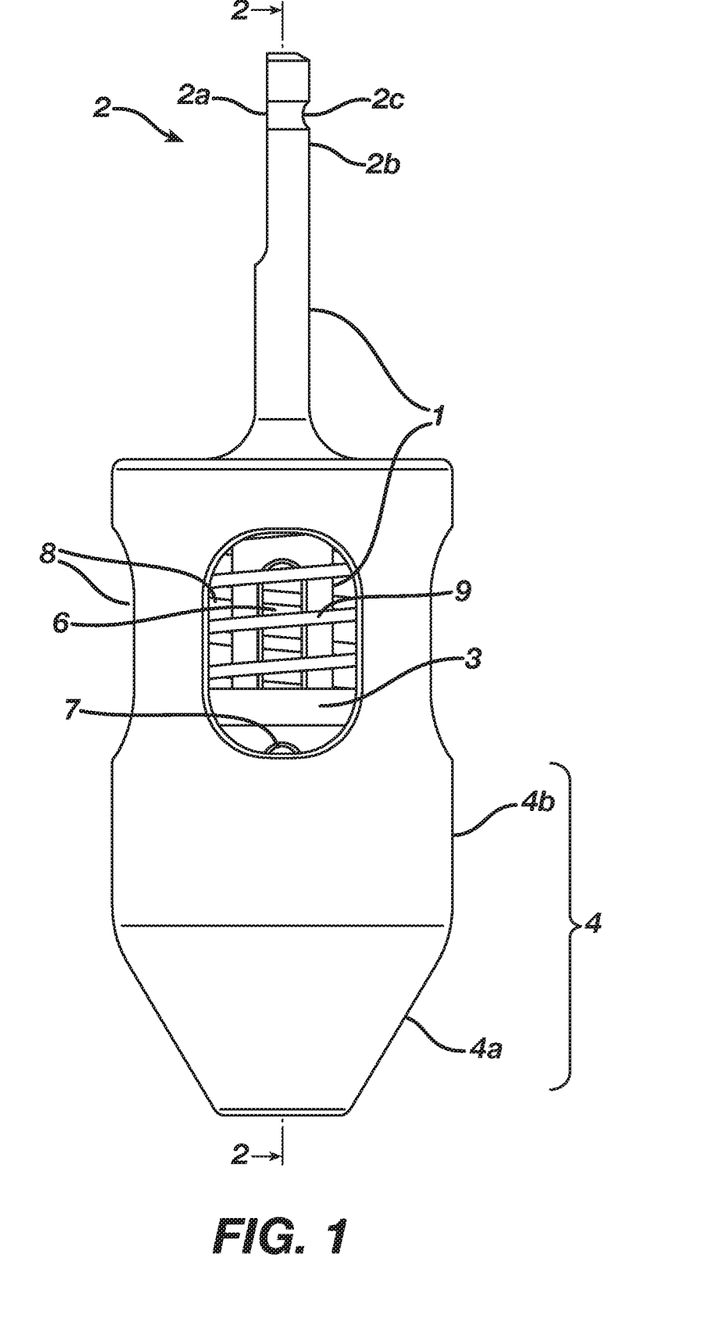
FIG. 1 shows a side view of a device for inserting a bone fixation pin.

Referring now to the drawings, in which like numerals refer to like components or steps, there are disclosed broad aspects of various exemplary embodiments. FIG. 1 is a side view of a device for inserting a bone fixation pin, having a housing 4 with a cylindrical proximal portion 4b and a distal portion 4a with a generally conical outer surface. Drive shaft 1 has a proximal end configured to engage a handle, and a distal end disposed within housing 4. Windows 8 may be positioned in the proximal portion 4b of housing 4.

The term "bone fixation pin," as used herein, refers to a pins, wires, screws, and other devices for insertion into bones to fix bone fragments in a desired relative orientation. Exemplary devices include Schanz pins, Steinmann pins, and Schanz screws.

In various embodiments, the proximal end of the drive shaft is configured to engage a handle with an Association for Osteosynthesis-style (AO) quick connect coupling, hereinafter referred to as an AO quick connect coupling. In such embodiments, the proximal end of the drive shaft has a male joint 2 with a planar surface 2a and a round surface 2b with a groove 2c therein. The male joint of the proximal end of the drive shaft engages a female joint on a handle, where the female joint has a corresponding planar surface which engages surface 2a, and a ball bearing or bearings which fit into groove 2c. When the planar surface in the female joint engages surface 2a, rotation of the drive shaft relative to the handle is prevented.

In various embodiments, the device for inserting a bone fixation pin includes a body 3, slidably disposed within housing 4. The outer diameter of body 3 is equal to an inner diameter of a proximal end 4b of housing 4, allowing body 3 to slidably move within the proximal end 4b of the housing. As seen in FIG. 1, body 3 is mounted on pin 7. Pin 7 is slidably disposed within slot 6 in drive shaft 1. A spring 9 biases body 3 toward the distal end 4a of housing 4. However, the inner surface of distal end 4a of housing 4 has a generally conical shape, which narrows in a distal direction. Due to the conical shape of the distal end 4a of housing 4, the inner surface of distal end 4a is narrower than body 3, preventing body 3 from entering the distal end 4a of housing 4. In some embodiments, the inner surface of distal end 4a of housing 4 may have a conical shape with a continuous slope. In some embodiments, the inner surface of distal end 4a of housing 4 may have a conical shape with a discontinuous slope or a plurality of steps.

Figure 2:
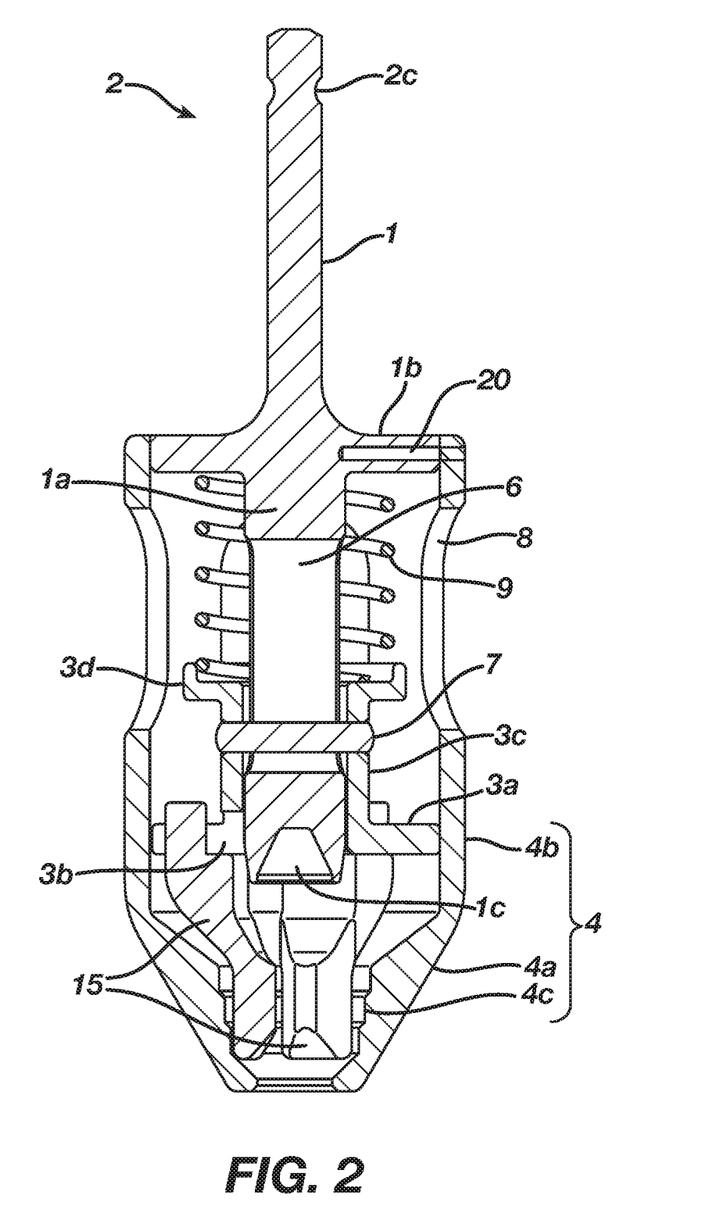
FIG. 2 shows a cross section view of the device for inserting a bone fixation pin of FIG. 1, in the direction of arrows 2 in FIG. 1.

FIG. 2 shows a cross sectional view of the device of FIG. 1, in the direction of arrows 2 of FIG. 1. The various parts include the drive shaft 1, the body 3, the housing 4, and a plurality of chuck arms 15. Drive shaft 1 includes a cylindrical portion 1a, a disc-shaped portion 1b having a diameter d, equal to an inner diameter d of housing 4, and a frusto-conical or conical opening 1c at a distal end of the drive shaft. The disc-shaped portion 1b of drive shaft 1 is fixed to housing 4 by pin 20. Housing 4 has a cylindrical distal portion 4b, a conical proximal portion 4a, and a stepped inner surface 4c. Body 3 has a ring-shaped portion 3a having an inner bore and radial slots 3b; a tubular member 3c, and second disc shaped member 3d at the proximal end of body 3. Radial slots 3b are each configured to slidably receive a chuck arm 15. Body 3 is fixed to pin 7, which is slidably mounted in slot 6 in drive shaft 1, allowing body 3 to move axially in the proximal portion 4b of housing 4, along drive shaft 1. Stepped inner surface 4c narrows in a distal direction, preventing body 3 from entering distal portion 4a of housing 4. Spring 9, mounted between disc shaped portion 1b of drive shaft 1 and disc shaped member 3d of body 3, biases the body 3 and the chuck arms 15 mounted in slots 3b toward the distal end of housing 4, so that the lower tips of chuck arms 15 are surrounded by stepped inner surface 4c.

Figure 3:
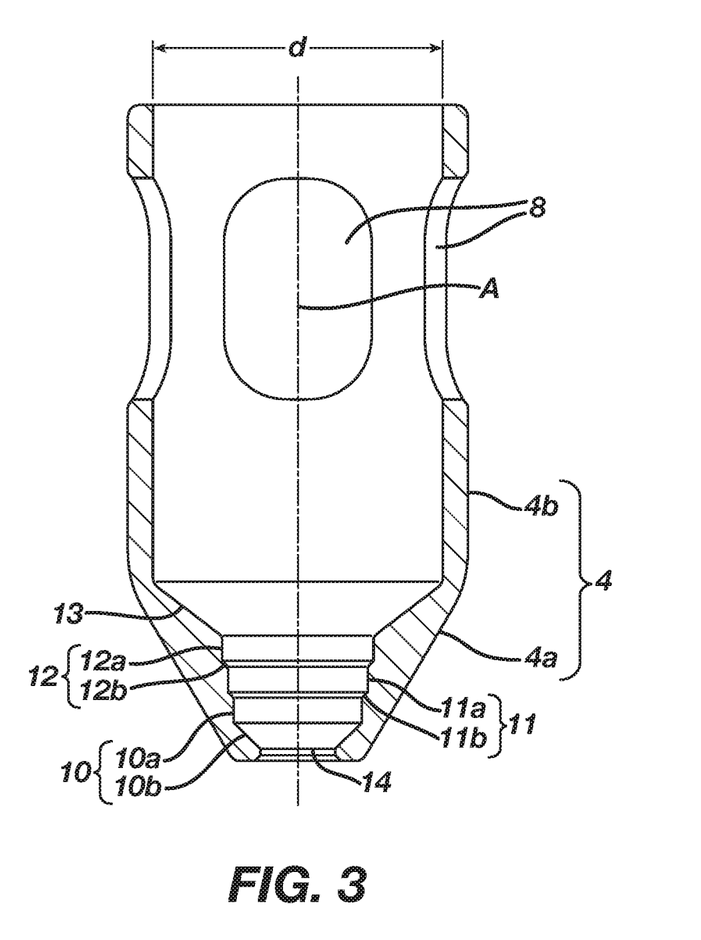
FIG. 3 shows a cross-sectional view of housing 4 of the device of FIG. 1.

FIG. 3 shows a cross-section of housing 4. Housing 4 has a proximal portion 4b, the proximal portion 4b having an inner surface with a diameter d, and a conical portion 4a. Conical portion 4a of housing 4 has a stepped inner surface, where a stepped surface is defined herein as a surface having multiple steps. As seen in FIG. 3, the housing may have an inner surface with three steps 10, 11, and 12, corresponding to stepped inner surface 4c as shown in FIG. 2. The step nearest the distal end of the housing, step 10, has a lower surface 10b sloped toward an axis A of housing 4, and a cylindrical inner surface 10a which is parallel to axis A. Lower surface 10b surrounds an opening 14 configured to receive a bone fixation pin. A second step in housing 4, step 11, has a lower surface 11b sloped toward surface 10a, and a cylindrical inner surface 11a which is parallel to axis A, and has a greater diameter than surface 10a. A third step 12 has a lower surface 12b sloped toward surface 11a, and a cylindrical inner surface 12a having a greater diameter than surface 11a. The upper edge of surface 12a meets a conical surface 13 between the stepped surface and the inner surface of the proximal portion 4b of housing 4. While FIG. 3 shows three steps 10, 11, and 12, the device for inserting a bone fixation pin may have a housing with only two steps on the inner surface of distal portion 4a, or with four, five, or more steps on the inner surface of distal portion 4a. Each of the different steps accommodates a different sized bone fixation pin.

Figure 4:
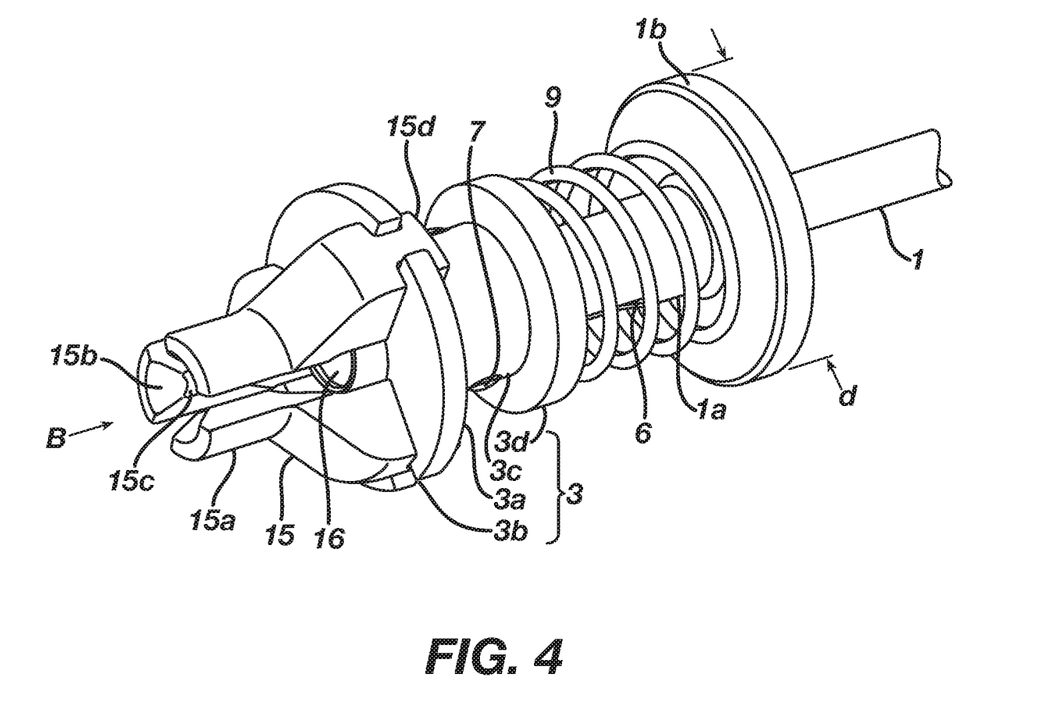
FIG. 4 shows a perspective view of the parts of the device of FIG. 1, with housing 4 removed.

FIG. 4 shows the mechanism of the device for inserting a bone fixation pin, with housing 4 removed for clarity. Drive shaft 1 includes a cylindrical portion 1a, a disc-shaped portion 1b having a diameter d, equal to the inner diameter d of housing 4, and a frustoconical or conical opening 1c at a distal end of the drive shaft. Opening 1c is configured to receive the rounded, conical, or frustoconical end of a bone fixation pin. Body 3 includes a ring-shaped portion 3a having an inner bore at the distal end of body 3. The outer diameter of the ring-shaped member 3a is d, equal to the inner diameter d of housing 4. The inner diameter of the ring shaped member 3a is configured to slidably engage the distal end of drive shaft 1. Disc shaped member 3a of body 3 has a plurality of slots 3b, each configured to slidably receive a chuck arm 15. A second disc shaped member 3d is at the proximal end of body 3, separated by a tubular member 3c. The drive shaft 1 passes through a common bore through member 3a, tubular member 3c, and member 3b. Spring 9 is mounted between the disc-shaped portion 1b of drive shaft 1 and disc shaped member 3d on body 3. Spring 9 biases body 3 toward the distal end of housing 4, away from the disc-shaped portion 1b of drive shaft 1, which is fixed at the proximal end of housing 1. Body 3 is mounted on pin 7 passing through slot 6 in drive shaft 1 and is able to move axially along drive shaft 1.

A plurality of chuck arms 15 are mounted on body 3, in the radial slots 3b on disc shaped member 3d. A T-shaped tab 15d on each chuck arm 15 fits into one of the slots 3b, allowing the chuck arms to move radially on body 3. Each chuck arm 15 has a tip with a generally pie-shaped cross section. The tip of each chuck arm 15 has a curved outer surface 15a, shaped as a segment of a right cylinder. The tip of each chuck arm 15 has an inner surface 15b which is slanted inwardly, so that the surfaces 15b on check arms 15 collectively form a conical or frustoconical space adapted to receive a conical or frustoconical head of a bone fixation pin, inserted in the direction of arrow B. As the pin moves in the direction of arrow B, force is exerted against surfaces 15b of chuck arms 15, causing the chuck arms to push body 3 in a proximal direction, against the biasing force applied by spring 9. The force exerted against surfaces 15b of chuck arms 15 may also cause chuck arms 15 to move outwardly in a radial direction along slots 3b, until chuck arms 15 have separated sufficiently to allow the conical or frustoconical head of the pin to pass the surfaces 15b of the chuck arms. At this point, planar surfaces 15c on the chuck arms 15 engage the body of the bone fixation pin. The pin slides along surfaces 15c until the head of the pin enters opening 1c on drive shaft 1. Once it becomes necessary to remove the pin from the chuck arms, the pin may be withdrawn axially from opening 14 in housing 4. Spring 9 then drives body 3 toward the distal end of housing 4, causing chuck arms 15 to move radially inward along the stepped inner surface of housing 4. Chuck arms 15 are then configured to engage a second pin having the same diameter as, or a different diameter from, the first pin.

Figure 5:
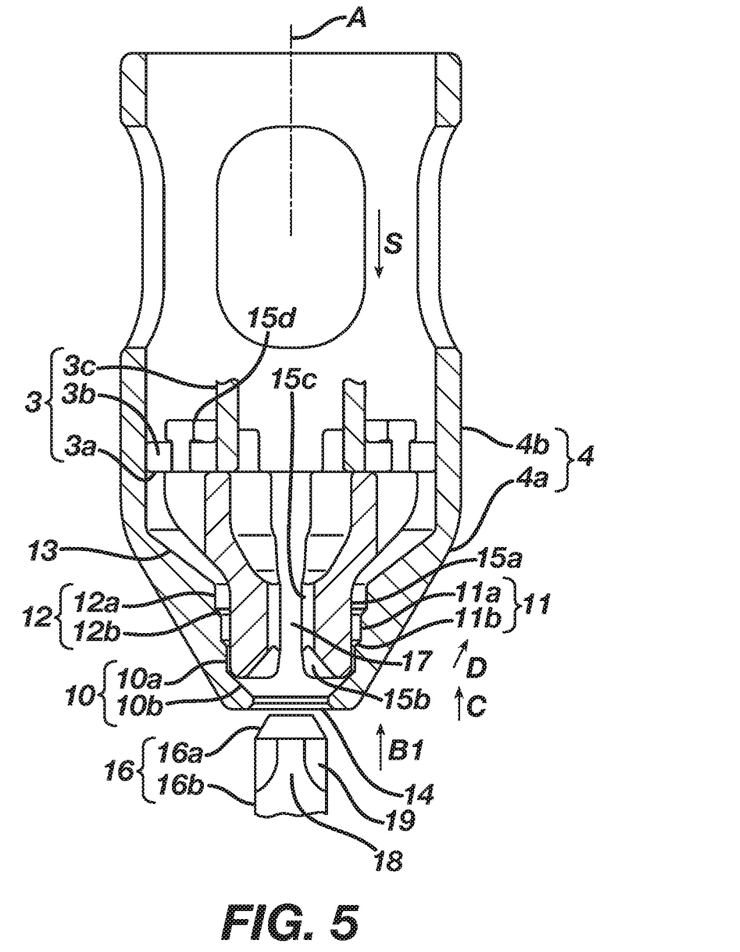
FIG. 5 shows a cross-sectional view of housing 4 of the device of FIG. 1, illustrating positioning of chuck arms 15 therein.

FIG. 5 shows housing 4, two chuck arms 15 and body 3 positioned within housing 4, and a bone fixation pin 16 entering housing 4 through opening 14 in the direction of arrow B1. As seen in FIG. 5, the outer surface 15a of each chuck arm forms a section of a cylinder which is coaxial with axis A of housing 4. In the position shown in FIG. 5, outer surface 15a of each chuck arm rests against cylindrical inner surface 10a of step 10 in housing 4. Cylindrical inner surface 10a constrains chuck arms 15, preventing outward radial movement of the chuck arms in slots 3b of the body 3. Spring force applied by spring 9 (shown in FIG. 4) in the direction of arrow S biases body 3, holding chuck arms 15, against axial movement. The bone fixation pin may have a tubular outer surface along the length of pin 16, with planar surfaces 19 near the proximal end of pin 16. As the pin is inserted into the space 17 defined by planar surfaces 15c of chuck arms 15, planar surfaces 19 engage planar surfaces 15c, preventing rotation of pin 16 relative to chuck arms 15.

When bone fixation pin 16 is pushed through opening 14 in housing 4, the head 16a of pin 16 contacts inner surfaces 15b of chuck arms 15. Since inner surface 10a prevents radial movement of chuck arms 15, force applied by pin 16 pushes chuck arms axially against spring force S, in the direction of arrow C. Once the outer surfaces 15a of chuck arms 15 move axially until they pass surface 10a, the constraint against radial movement is released. Chuck arm surfaces 15a then slide along surface 11b of step 11 in the direction of arrow D, moving both axially against spring force S and radially along slot 3b in body 3. Radial movement continues until outer surfaces 15a of chuck arms 15 contact inner surface 11a of step 11, at which point surface 11a constrains chuck arms 15 against further radial movement, expanding an opening 17 defined by planar surfaces 15c of chuck arms 15. If opening 17 is large enough to accommodate the tubular body 16b of pin 16, body 16b enters space 17 and planar surfaces 19 on pin 16 are engaged by chuck arm surfaces 15c. If opening 17 is too small to accommodate tubular body 16b, pin 16 pushes chuck arms axially until they pass surface 11a and move radially until the outer surfaces 15a of chuck arms 15 engage surface 12a of housing 4, causing opening 17 to expand to accommodate tubular body 16b. Thus, the device disclosed herein is configured to engage bone fixation pins or screws having different diameters.

Figure 6:
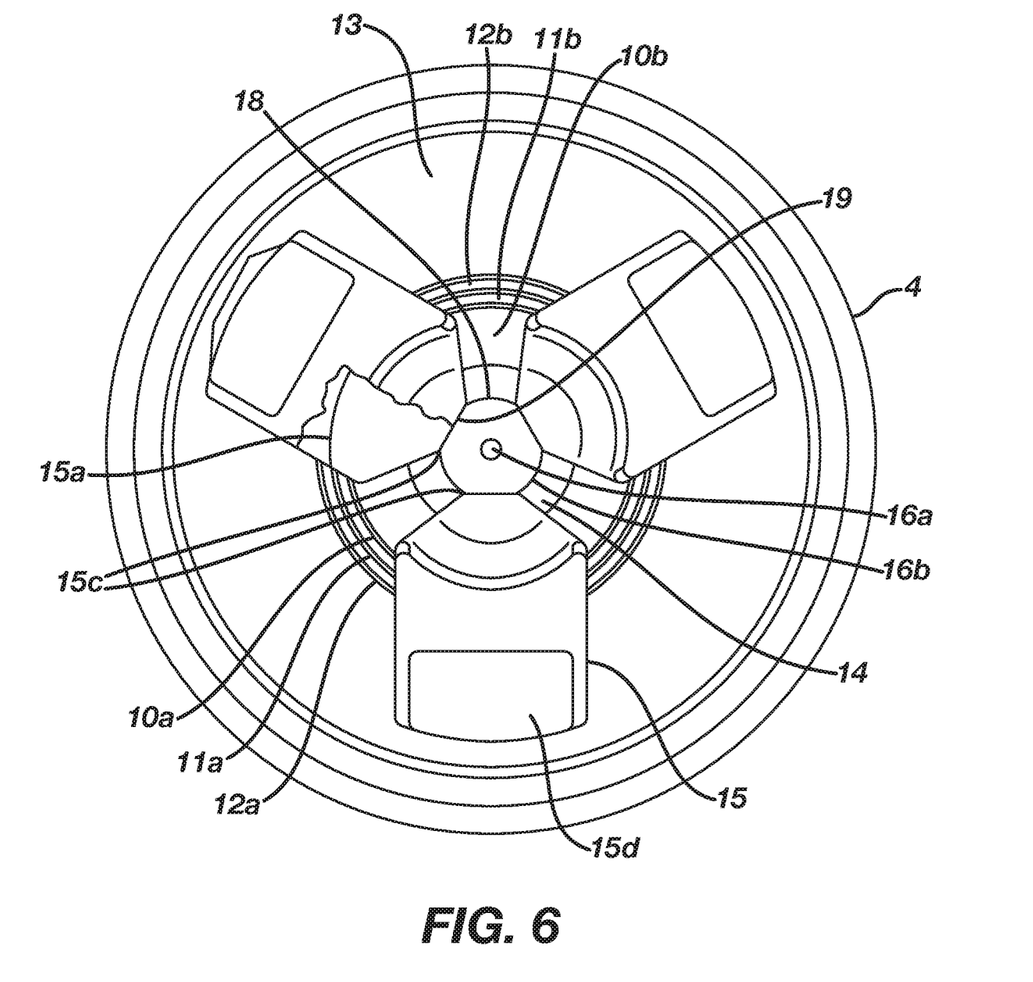
FIG. 6 shows an interior view of housing 4 of the device of FIG. 1, illustrating positioning of chuck arms 15 therein.

FIG. 6 shows an end view of housing 4, showing positioning of chuck arms 15d within housing 4, when engaging bone fixation pin 16. One of the chuck arms 15 has been partially cut away to show the positioning of the lower tip of the chuck arm, relative to the stepped inner surface of housing 4. As seen in FIGS. 5 and 6, the upper portion of each chuck arm 15 occupies a space defined by body 3 at its upper end, and conical surface 13 of housing 4 at its lower end. The lower tip of each chuck arm 15 extends into the portion of housing 4 including steps 10, 11, and 12. As seen in FIG. 6, the body 16b of a bone fixation pin occupies a space defined by planar surfaces 15c of chuck arms 15, with planar surfaces 19 at the proximal end of pin body 16 engaging planar surfaces 15c to prevent rotation of the pin relative to the chuck arms. As seen in FIG. 6, the cutaway view of one of chuck arms 15 shows that the outer surface 15a of the tip of each chuck arm 15 rests against cylindrical inner surface 11a of housing 4, constraining the chuck arm against radial movement so that the bone fixation pin is securely gripped by the chuck arms 15. Once inserted into a bone, the bone fixation pins are removed from the device by withdrawing the pins axially out of hole 14 in housing 4.

Figure 7:
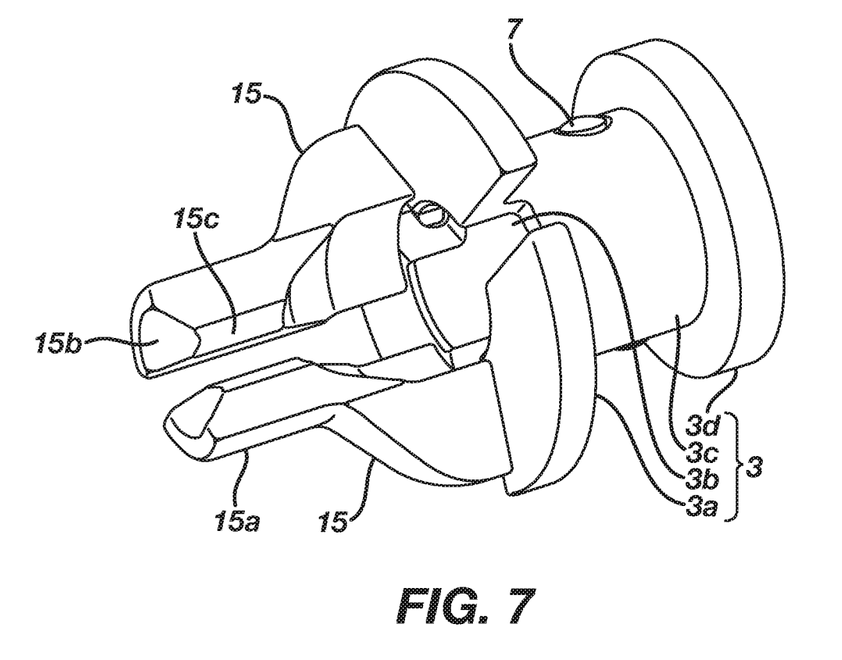
FIG. 7 shows a perspective view of the body of the device of FIG. 1, with two of the chuck arms 15 attached thereto.

FIG. 7 shows body 3 with chuck arms 15 mounted thereon, where one chuck arm has been removed to better show details of the construction of the body and the chuck arms. Each chuck arm 15 is mounted in a radial slot 3b on body 3, so it may move radially relative to the body. Tubular member 3b on body 3 is fixed to pin 7. A detailed view of chuck arms 15, showing the shapes of surfaces 15a. 15b, and 15c is presented in FIG. 7.

Figure 8:
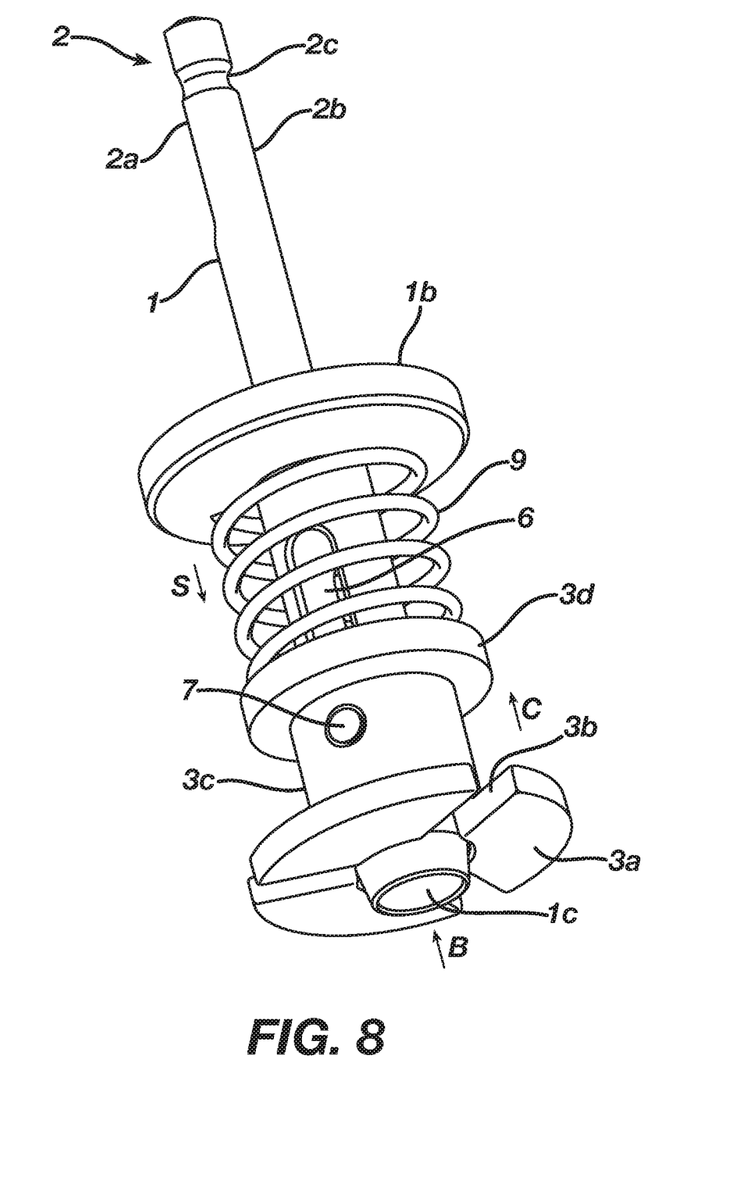
FIG. 8 shows a perspective view of the drive shaft of the device of FIG. 1.

FIG. 8 provides a view of drive shaft 1, with body 3 mounted thereon (body 3 shown in cross section). As discussed previously, the proximal end of the drive shaft 1 is configured to engage a handle with an AO quick connect coupling and has a male joint 2 with a planar surface 2a and a round surface 2b with a groove 2c therein. Tubular member 1b is fixed to the proximal end of housing 4. Pin 7, fixed to tubular portion 3b of body 3, is configured to slide axially in slot 6 on drive shaft 1. Opening 1c on drive shaft 1 receives the head of a bone fixation pin. As discussed previously, insertion of a bone fixation pin axially in the direction of arrow 4 causes body 3 to move in a proximal direction C in housing 4, against the spring force S applied by spring 9, until the head of the bone fixation pin engages opening 1c on drive shaft 1.

Figure 9:
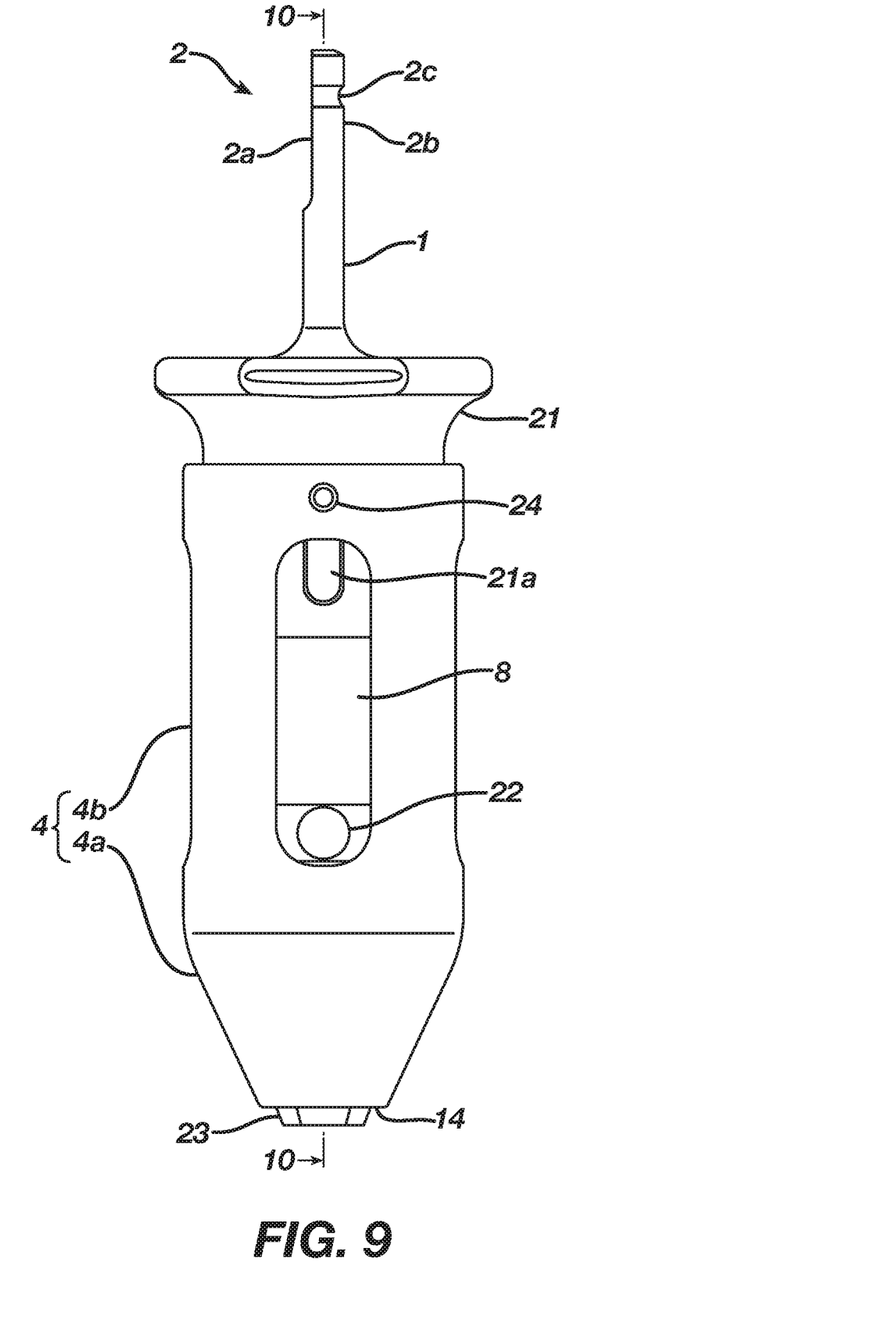
FIGS. 9 and 10 show views of an alternate embodiment of the device for inserting a bone fixation pin
Figure 10:
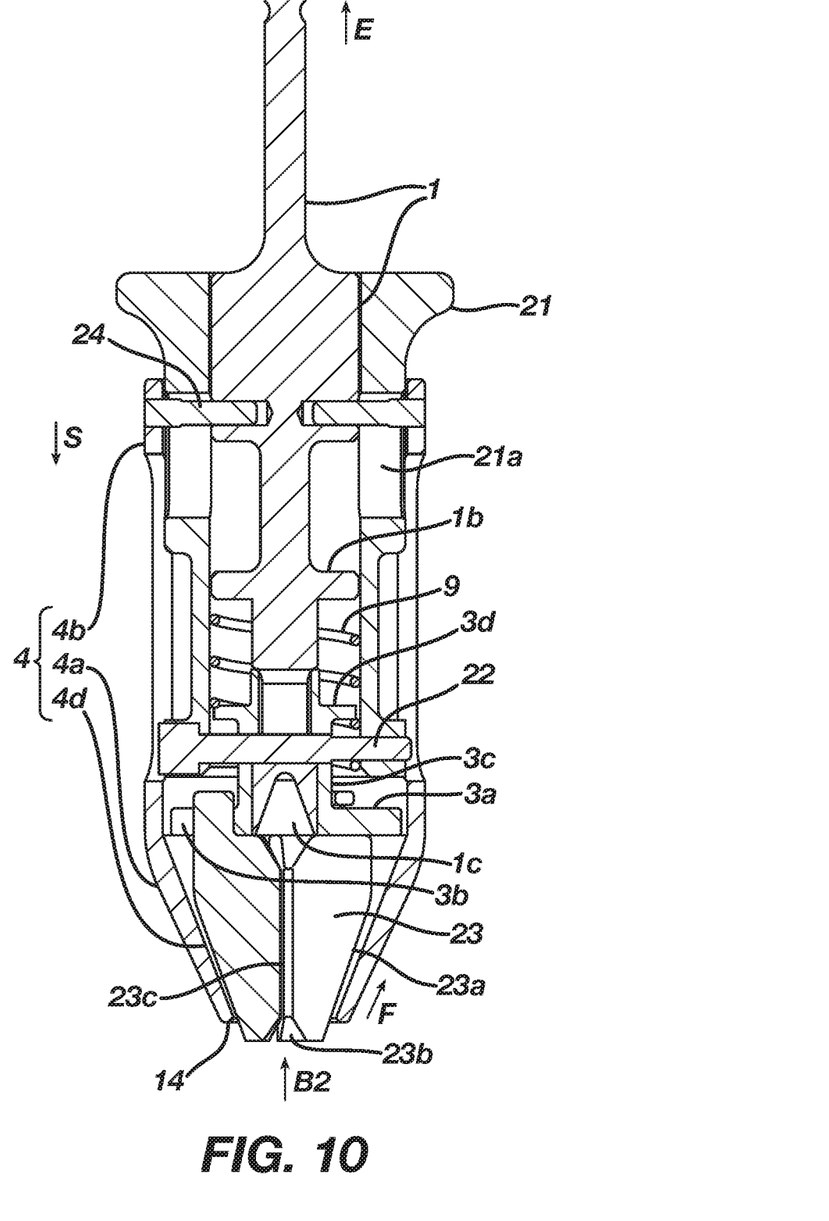

In an alternate embodiment shown in FIGS. 9 and 10, a device for inserting a bone fixation pin has a housing 4 with a cylindrical proximal portion 4b and a distal portion 4a with a generally conical outer surface. Windows 8 may be positioned in the proximal portion 4b of housing 4. The device has a drive shaft 1 with a proximal end configured to engage a handle, and a distal end disposed within housing 4. The proximal end of the drive shaft may be configured to engage a handle with an AO quick connect coupling. In such embodiments, the proximal end of the drive shaft has a male joint 2 with a planar surface 2a and a round surface 2b with a groove 2c therein. The male joint of the proximal end of the drive shaft engages a female joint on a handle, where the female joint has a corresponding planar surface which engages surface 2a. When the planar surface in the female joint engages surface 2, rotation of the drive shaft relative to the handle is prevented.

The device for inserting a bone fixation pin includes a body 3, slidably disposed within housing 4. The outer diameter of body 3 is equal to an inner diameter of housing 4. In the embodiment of FIGS. 9 and 10, body 3 is mounted on pin 7, in a similar fashion to the positioning of body 3 in the embodiment of FIG. 1. Pin 7 is slidably disposed within slot 6 in drive shaft 1. A spring 9 biases body 3 toward the distal end 4a of housing 4. The conical shape of the distal end 4a of housing 4 prevents body 3 from entering the distal end of housing 4, in a similar fashion to the stepped inner surface of the distal end of body 4 in the embodiment of FIG. 2. The drive shaft 1 passes through a bore in a tubular release member 21. Drive shaft 1 is fixed to housing 4 by pin 24. Pin 24 passes through slots 21a in release member 21, allowing release member 21 to move axially relative to housing 4 and drive shaft 1. Chuck arms 23 are visible at an opening 14 in housing 4.

As seen in FIG. 10, body 3 is positioned in housing 4. Body 3 has a ring-shaped portion 3a having an inner bore and radial slots 3b; a tubular member 3c, and a second disc shaped member 3d at the proximal end of body 3. Radial slots 3b are each configured to slidably receive a chuck arm 23. Pin 22 secures the body 3 to release member 21, so that body 3 and release member 21 may move axially within housing 4 as a unit. Spring 9 is mounted between a disc shaped portion 1b of drive shaft 1 and the disc shaped member 3d of body 3.

As seen in FIG. 10, housing 4 has a distal portion 4a with a generally conical inner surface 4d. Chuck arms 23 have a slanted outer surface 23a which slidably engages the conical inner surface 4d. If a bone fixation pin is inserted axially in a proximal direction into opening 14 of housing 4 in the direction of arrow B2, the head of the bone fixation pin, which may be rounded, conical, or frustoconical, engages a slanted inner surface 23b on each chuck arm 23. Application of force to surfaces 23b pushes the body 3 and the release member 21 in axially in the direction of arrow E, while surfaces 23a of chuck arms 23 slide along conical inner surface 4d of body 4, moving in the direction of arrow F. The spacing between chuck arms 23 expands as they move in the direction of arrow F, until the head of the bone fixation pin passes surface 23b on chuck arms 23, and the body of the bone fixation pin is engaged by inner surfaces 23c of chuck arm 23. The head of the bone fixation pin is then engaged by conical or frustoconical opening 1c in drive shaft 1. Spring force S biases body 3 in a proximal direction, and therefore biases chuck arms 15 to move proximally, along conical surface 4d toward an axis of housing 4. If a bone fixation pin is between chuck arms 23, the force applied by spring 9 biases chuck arms 23 against the pin, maintaining a grip on the pin.

If the release member 21 is pulled in the direction of arrow E prior to inserting a pin, body 3 is pulled and chuck arms 23 are moved in a proximal direction. This releases the constraint on motion of the chuck arms applied by housing inner surface 4d, increasing the spacing between chuck arms 23 so a bone fixation pin may be inserted directly between the chuck arms 23. Releasing member 21 allows the spring 9 to move body 3 and chuck arms 23 in a distal direction, causing chuck arms to grip the bone fixation pin. If the release member 21 is pulled in the direction of arrow E while a pin is engaged by chuck arms 23, the force applied by spring 9 biasing chuck arms 23 against the pin is released, allowing ready removal of the bone fixation pin.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. An apparatus for inserting a bone fixation pin having a head and a cylindrical body having a body diameter, said apparatus comprising:
    a housing having a proximal portion and a distal portion, the distal portion having a stepped inner surface and an opening configured to receive the bone fixation pin;
    a drive shaft having a proximal end configured to engage a handle and a distal end;
    a body having an axis and a peripheral edge, said body comprising:
        a bore along the axis, said bore being configured to slidably engage the distal end of the drive shaft; and
        a plurality of spaced slots in the peripheral edge of the body; and
    a plurality of chuck arms, each chuck arm being configured to move radially along one of the spaced slots in the peripheral edge of the body, each chuck arm having an inner surface and a lower tip;
    wherein:
    the distal end of the drive shaft and the body are within the proximal portion of the housing, said body being biased toward the distal end of the housing;
    wherein the inner surface of each chuck arm is configured to engage the bone fixation pin, and the lower tip of each chuck arm slidably engages a first step on the stepped inner surface of the housing.

2. The apparatus of claim 1, wherein the distal end of the drive shaft has a conical or frustoconical opening configured to receive the conical or frustoconical head of the bone fixation pin.

3. The apparatus of claim 2, wherein the apparatus is configured to receive a bone fixation pin through the opening in the housing until the head of the pin engages the opening in the distal end of the drive shaft;
    wherein contact between the conical or frustoconical head of the bone fixation pin and the sloped lower surfaces of the chuck arms pushes the chuck arms toward the proximal end of the housing; and
    wherein the lower tip of each chuck arm is configured to disengage from the first step on the stepped inner surface of the housing and engage a second step on the stepped inner surface as the chuck arms move toward the proximal end of the housing;
    wherein the chuck arms are configured to engage the cylindrical body of the bone fixation pin when the lower tip of each chuck arm engages the second step on the stepped inner surface.

4. The apparatus of claim 1, wherein the inner surface of the chuck arm comprises a sloped lower surface configured to engage the conical or frustoconical head of the bone fixation pin; and an upper surface parallel to the axis of the body;
    said the upper surface being configured to engage the cylindrical body of the bone fixation pin.

5. The apparatus of claim 4, wherein the stepped inner surface of the housing comprises a second step and a third step, said second step and said third step being configured to be sequentially engaged by the lower tip of each chuck arm as the chuck arms move toward the proximal end of the housing;
    wherein the chuck arms are configured to engage the cylindrical body of a bone fixation pin having a first body diameter when the lower tip of each chuck arm engages the second step on the stepped inner surface; and
    wherein the chuck arms are configured to engage the cylindrical body of a bone fixation pin having a second body diameter when the lower tip of each chuck arm engages the third step on the stepped inner surface.

6. The apparatus of claim 1, wherein the body is biased toward the distal end of the housing by a spring.

7. The apparatus of claim 1, wherein each chuck arm has a planar inner surface;
    wherein the bone fixation pin has an axis, and a plurality of planar surfaces on the head of the bone fixation pin, extending in a direction parallel to the axis of the bone fixation pin, and
    wherein each planar surface on the head of the bone fixation pin engages the planar inner surface on one of the chuck arms.

* * * * *